(12) United States Patent
Arcella et al.

(10) Patent No.: US 6,566,471 B1
(45) Date of Patent: *May 20, 2003

(54) PEROXIDE CURABLE FLUOROELASTOMERS PARTICULARLY SUITABLE FOR MANUFACTURING O-RINGS

(75) Inventors: Vincenzo Arcella, Novara (IT); Giulio Brinati, Milan (IT); Margherita Albano, Milan (IT); Vito Tortelli, Milan (IT)

(73) Assignee: Ausimont S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 08/879,319

(22) Filed: Jun. 19, 1997

Related U.S. Application Data

(62) Division of application No. 08/723,928, filed on Oct. 1, 1996, now Pat. No. 5,674,959, which is a division of application No. 08/441,218, filed on May 15, 1995, now Pat. No. 5,625,019.

(30) Foreign Application Priority Data

May 18, 1994 (IT) .......................................... MI94A0998

(51) Int. Cl.$^7$ ............................................. C08F 216/12
(52) U.S. Cl. ....................................................... 526/247
(58) Field of Search ................................ 526/247, 249, 526/206

(56) References Cited

U.S. PATENT DOCUMENTS

| | | | |
|---|---|---|---|
| 3,810,874 A | | 5/1974 | Mitsch et al. |
| 4,035,565 A | * | 7/1977 | Apotheker et al. |
| 4,243,770 A | | 1/1981 | Tatemoto et al. ............ 525/331 |
| 4,543,394 A | * | 9/1985 | Finlay et al. ................ 526/249 |
| 4,612,357 A | | 9/1986 | Bekiarian et al. ........... 526/247 |
| 4,745,165 A | * | 5/1988 | Arcella et al. |
| 4,864,006 A | | 9/1989 | Giannetti et al. ........... 526/209 |
| 4,948,852 A | * | 8/1990 | Moore |
| 4,948,853 A | * | 8/1990 | Logothetis |
| 4,973,633 A | * | 11/1990 | Moore ........................ 526/247 |
| 4,973,634 A | * | 11/1990 | Logothetis |
| 4,983,697 A | * | 1/1991 | Logothetis |
| 5,032,655 A | * | 7/1991 | Moore |
| 5,037,921 A | * | 8/1991 | Carlson |
| 5,151,492 A | | 9/1992 | Abe et al. ................... 526/206 |
| 5,162,468 A | * | 11/1992 | Babb et al. ................. 526/247 |
| 5,173,553 A | * | 12/1992 | Albano et al. |
| 5,219,964 A | * | 6/1993 | Albano et al. .............. 526/247 |
| 5,225,504 A | * | 7/1993 | Tatsu et al. ................. 526/247 |
| 5,231,154 A | * | 7/1993 | Hung ......................... 526/254 |

FOREIGN PATENT DOCUMENTS

| | | | |
|---|---|---|---|
| EP | 0136596 | 4/1985 | |
| EP | 0153848 | * 9/1985 | ................ 526/247 |
| EP | 0171290 | * 2/1986 | ................ 526/249 |
| EP | 0200908 | 12/1986 | |
| EP | 0410351 | 1/1991 | |
| EP | 0525685 | 2/1993 | |
| EP | 0625526 | 11/1994 | |
| FR | 1410444 | 12/1965 | |

OTHER PUBLICATIONS

Masato Yoshida et al, Recent Progress in Perfluoralkylation by Radical Species With Special Reference to the Use of Bis(Perfluoroalkanoyl Peroxides, *J. Fluorine Chemistry*, 49 (1990),pp. 1–20.

Wei–Huan Huang, Reactions With Aromatic and Heteroromatic Compounds (may be only a partial title), *J.Fluorine Chemistry*, 58 (1992), pp. 1–8.

V. Tortelli et al, Telomerization of Tetrafluorethylene and Hexafluoropropene: Synthesis of Diiodoperfluoroalkanes,*J. Fluorine Chemistry*, 47 (1990), pp. 199–217.

\* cited by examiner

*Primary Examiner*—Fred Zitomer
(74) *Attorney, Agent, or Firm*—Arent Fox Kintner Plotkin & Kahn

(57) ABSTRACT

New fluoroelastomers are described, having iodine atoms in terminal position and monomeric units in the chain deriving from an iodinated olefin of formula:

$$CHR=CH-Z-CH_2CHR-I \qquad (I)$$

wherein: R is —H or —$CH_3$; Z is a (per)fluoroalkylene radical $C_1-C_{18}$, linear or branched, optionally containing one or more ether oxygen atoms, or a (per) fluoropolyoxyalkylene radical. These products, upon peroxide curing, require extremely short post-curing treatments (around 30–60 minutes at 180°–230° C.) and are characterized by compression set values lower than 25% (measured on O-rings at 200° C. for 70 hours according to ASTM Standard D395 Method B).

9 Claims, No Drawings

PEROXIDE CURABLE FLUOROELASTOMERS PARTICULARLY SUITABLE FOR MANUFACTURING O-RINGS

Division of Ser. No. 08/723,928, Oct. 1, 1996, U.S. Pat. No. 5,674,959, which is A Division of Ser. No. 08/441,218, May 15, 1995, U.S. Pat. No. 5,625,019.

The present invention relates to new peroxide curable fluoroelastomers particularly suitable for manufacturing O-rings.

Various types of fluoroelastomers are known in the art, widely used in all those fields where superior elastic properties associated with high thermochemical stability are required. For a wide survey on such products see for instance "Ullmann's Encyclopedia of Industrial Chemistry", vol. A-11, pag. 417–429 (1988, VCH Verlagsgesellschaft).

It is also known that for manufacturing sealing elements, particularly O-rings, it is necessary to use elastomers endowed with particularly low compression set values. In fact, O-ring sealing effectiveness is as better as the article, upon compression, is able to recover initial dimensions. Since the fluoroelastomers are used in a wide temperature range, compression set values should be low not only at low temperatures, but also at high temperatures. Compression set values (measured at 200° C. for 70 hours, according to ASTM Standard D395, Method B) lower than 25% are generally required. More particularly, military specifications (MIL-R-83248B) asks for O-rings having a maximum compression set value of 20% (measured at 200° C. for 70 hours as well).

Fluoroelastomers which can meet such requirements are those curable ionically, which need addition of curing agents (for instance polyhydroxy compounds, such as Bisphenol AF or Bisphenol A), of suitable accelerators (for instance ammonium, phosphonium or amino-phosphonium salts), and of divalent metal oxides and/or hydroxides (for instance MgO, Ca(OH)$_2$). Elastomers of this type are described for instance in patent application EP-525,685. However, ionic curing shows some drawbacks, among which the fact that a post-curing treatment is needed, generally carried out at 200°–260° C. for 12–24 hours, in order to complete curing, and to eliminate volatile by-products, so as to improve and stabilize mechanical and elastic properties. This implies a remarkable increase in processing times and costs and therefore strongly limits the possibilities of large scale production.

As described in U.S. Pat. No. 4,243,770, fluoroelastomers can be crosslinked also by means of peroxides. To such purpose it is necessary to carry out the polymerization in the presence of suitable iodinated chain transfer agents, which introduce into the macromolecules iodine atoms in terminal position: in the presence of radicals deriving from a peroxide said iodine atoms act as cure sites in consequence of homolitic breakage of the C—I bonds. Fluoroelastomers of this type generally do not require long post-curing treatments: in some cases it is sufficient a post-curing in air at about 200°–230° C. for 1–4 hours. However, such products do not meet the specifications indicated above for O-ring manufacturing: the compression set value is indeed usually high, at least equal to 28–30% or higher.

The Applicant has now found a new class of fluoroelastomers as defined hereinunder, which, upon peroxide curing, need extremely short post-curing treatments (around 30–60 minutes at 180°–230° C.) and are characterized by compression set values lower than 25% (measured on O-rings at 200° C. for 70 hours according to ASTM Standard D395 Method B).

Therefore, a first object of the present invention are peroxide curable fluoroelastomers, having iodine atoms in terminal position, and monomeric units in the chain deriving from an iodinated olefin of formula:

$$CHR\!=\!CH\!-\!Z\!-\!CH_2CHR\!-\!I \qquad (I)$$

wherein: R is —H or —CH$_3$; Z is a C$_1$–C$_{18}$ (per)fluoroalkylene radical, linear or branched, optionally containing one or more ether oxygen atoms, or a (per)fluoropolyoxyalkylene radical.

Further objects of the present invention are the iodinated olefins of formula (I), and the preparation process thereof, as described hereinunder.

As regards formula (I), Z is preferably a C$_4$–C$_{12}$ perfluoroalkylene radical, or a (per)fluoropolyoxyalkylene radical of formula:

$$-(Q)_p\!-\!CF_2O\!-\!(CF_2CF_2O)_m(CF_2O)_n\!-\!CF_2\!-\!(Q)_p\!- \qquad (II)$$

wherein: Q is a C$_1$–C$_6$, preferably C$_1$–C$_3$, alkylene or oxyalkylene radical; p is 0 or 1; m and n are numbers such that the m/n ratio is from 0.2 to 5 and the molecular weight of said (per)fluoropolyoxyalkylene radical is from 400 to 10,000, preferably from 500 to 1,000. Preferably, Q is selected from: —CH$_2$O—; —CH$_2$OCH$_2$—; —CH$_2$—; —CH$_2$CH$_2$—.

The olefins of formula (I) can be prepared starting from compounds of formula I—Z—I according to the following process:

(1) adding ethylene or propylene to a compound of formula I—Z—I, thus obtaining a diiodinated product of formula:

$$I\!-\!CHR\!-\!CH_2\!-\!Z\!-\!CH_2\!-\!CHR\!-\!I \qquad (III)$$

where R and Z are defined as above;

(2) partially dehydroiodinating the product of formula (III) with a base (for instance NaOH, KOH, tertiary amines, etc.), so as to obtain the iodinated olefin of formula (I).

As to step (1), the addition of ethylene or propylene is usually carried out in the presence of suitable catalysts, such as redox systems, for instance CuI or FeCl$_3$, in solution in an organic solvent, for instance acetonitrile. The addition reaction between a perfluoroalkyliodide and an olefin is described, for instance, by M. Hudliky in "Chemistry of Organic Fluorine Compounds" (2nd Edition, Ellis Horwood Ltd., Chichester, 1976), and by R. E. Banks in "Organofluorine Chemicals and Their Industrial Applications" (Ellis Horwood Ltd. Chichester, 1979), or in J. Fluorine Chemistry, 49 (1990), 1–20 and in J. Fluorine Chemistry, 58 (1992), 1–8.

The dehydroiodination reaction of step (2) can be carried out either without any solvent, or by dissolving the diiodinated product in a suitable solvent (for instance a glycol such as diethylenglycol, or a long chain alcohol). To maximize the iodinated olefin yield, avoiding as far as possible a further dehydroiodination reaction with formation of the corresponding bis-olefin of formula CHR=CH—Z—CH=CHR, it is possible:

(a) to employ the base in defect with respect to the stoichiometric amount, with a molar ratio base/diiodinated compound preferably from 1.5 to 0.5, and then separating the iodinated olefin from the bis-olefin by fractional distillation; or (b) to carry out the dehydroiodination reaction at reduced pressure, so as to remove she iodinated olefin from the reaction mixture as it forms, taking advantage of the fact that the latter has a boiling point lower than that of the starting diiodinated product; in such a case the reaction is preferably carried out without any solvent.

Alternatively, it is possible to carry out step (1) in defect of ethylene or propylene, to favour as much as possible formation of mono-addition product I—Z—CH$_2$—CHR—I (which can be separated from the di-addition product by fractional distillation); the mono-addition product is then dehydroiodinated as described above, with formation of olefin I—Z—CH=CHR, which is finally submitted to a further addition of ethylene or propylene to give the iodinated olefin I—CHRCH$_2$—Z—CH=CHR.

When Z is a (per)fluoroalkylene radical, optionally containing one or more ether oxygen atoms, the starting diiodinated compound I—Z—I can be obtained by telomerization of a (per)fluoroolefin C$_2$–C$_4$ or of a (per)fluorovinylether C$_3$–C$_8$ (for instance tetrafluoroethylene, perfluoropropene, vinylidene fluoride, perfluoromethylvinylether, perfluoro-propylvinylether, or mixtures thereof), by using a product of formula I—(R$_f$)$_k$—I (where k=0, 1; R$_f$=C$_1$–C$_8$ (per)fluoroalkylene radical) as telogenic agent. Telomerization reactions of this type are described, for instance, by C. Tonelli and V. Tortelli in J. Fluorine Chem., 47 (1990), 199, or also in EP-200,908.

When Z is a (per)fluoropolyoxyalkylene radical, the preparation of the products I—Z—I is described, for instance, in U.S. Pat. No. 3,810,874.

The amount of monomeric units deriving from the iodinated olefin of formula (I) present in the fluoroelastomers object of the present invention is generally from 0.01 to 1.0 moles, preferably from 0.03 to 0.5 moles, even more preferably from 0.05 to 0.2 moles, per 100 moles of the other basic monomeric units.

The total iodine amount in the fluoroelastomers object of the present invention is, on the average, from 1.8 to 5.0, preferably from 2.0 to 4.0, iodine atoms per chain. The average number of iodine atoms per chain in terminal position is in turn generally from 1.0 to 2.0, preferably from 1.5 to 1.8. The iodine atoms in terminal position can be introduced, as described in U.S. Pat. No. 4,243,770, by adding during polymerization iodinated chain transfer agents, such as for instance compounds of formula R$_f$T$_x$, wherein R$_f$ is a (per)fluoroalkyl or a (per)fluorochloroalkyl having from 1 to 8 carbon atoms, while x in 1 or 2. In particular, the iodinated chain transfer agent can be selected from: 1,3-diiodoperfluoropropane, 1,4-diiodoperfluorobutane, 1,6-diiodoperfluorohexane, 1,3-diiodo-2-chloroperfluoropropane, 1,2-di(iododifluoromethyl)-perfluorocyclobutane, monoiodoperfluoroethane, monoiodoperfluorobutane, 2-iodo-1-hydroperfluoroethane, etc. Particualrly preferred are diiodinated chain transfer agents (x=2). Alternatively, it is possible to use as chain transfer agents alkali or alkaline-earth metal iodides, as described in U.S. Pat. No. 5,173,553. The amount of chain transfer agent to be added to the reaction medium is chosen according to the molecular weight which is intended to be obtained and to the chain transfer agent effectiveness.

The basic structure of the fluoroelastomers object of the present invention can be selected in particular from:

(1) VDF-based copolymers, where VDF is copolymerized with at least a comonomer selected from: perfluoroolefins C$_2$–C$_8$, such as tetrafluoroethylene (TFE), hexafluoropropene (HFP); C$_2$–C$_8$ chloro- and/or bromo-fluoroolefins, such as chlorotrifluoroethylene (CTFE) and bromotrifluoro-ethylene; (per)fluoroalkylvinylethers (PAVE) CF$_2$=CFOR$_f$, wherein R$_f$ is a C$_1$–C$_6$ (per)fluoroalkyl, for instance trifluoromethyl, bromodifluoromethyl, pentafluoropropyl; (per)fluoro-oxyalkylvinylethers CF$_2$=CFXO, where X is a C$_1$–C$_{12}$ perfluoro-oxyalkyl having one or more ether groups, for instance perfluoro-2-propoxypropyl; C$_2$–C$_8$ non-fluorinated olefins (Ol), for instance ethylene and propylene; typical compositions are the following: (a) VDF 45–85%, HFP 15–45%, TFE 0–30%; (b) VDF 50–80%, PAVE 5–50%, TFE 0–20%; (c) VDF 20–30%, Ol 10–30%, HFP and/or PAVE 18–27%, TFE 10–30%;

(2) TFE-based copolymers, where TFE is copolymerized with at least a comonomer selected from: (per)fluoroalkylvinylethers (PAVE) CF$_2$=CFOR$_f$, where R$_f$ is defined as above; (per)fluoro-oxyalkylvinylethers CF$_2$=CFOX, wherein X is defined as above; C$_2$–C$_8$ fluoroolefins containing hydrogen and/or chlorine and/or bromine atoms; C$_2$–C$_8$ non-fluorinated olefins (Ol); typical compositions are the following: (d) TFE 50–80%, PAVE 20–50%; (e) TFE 45–65%, Ol 20–55%, VDF 0–30%; (f) TFE 32–60%, Ol 10–40%, PAVE 20–40%; (g) TFE 33–75%, PAVE 15–45%, VDF 10–22%.

The preparation of the fluoroelastomers object of the present invention can be carried out by copolymerization of the monomers in aqueous emulsion according to methods well known in the art, in the presence of radical initiators (for instance alkali metal or ammonium persulphates, perphosphates, perborates or percarbonates), optionally in combination with ferrous, cuprous or silver salts or other easily oxidable metals. In the reaction medium are usually present also surfactants of various types, among which particularly preferred are the fluorinated surfactants of formula:

wherein R$_f$ is a C$_5$–C$_{16}$ (per)fluoroalkyl chain or a (per)fluoropolyoxyalkylene chain, X$^-$ is —COO$^-$ or —SO$_3^-$, M$^+$ is selected from: H$^+$, NH$_4^+$, alkali metal ion. Among the most commonly used, we can cite: ammonium perfluorooctanoate, (per)fluoropolyoxyalkylenes terminated with one or more carboxyl groups, etc.

In a preferred embodiment, the fluoroelastomers object of the present invention are prepared in the presence of an aqueous microemulsion of perfluoropolyoxyalkylenes, as described in U.S. Pat. No. 4,864,006, or in the presence of an aqueous microemulsion of fluoropolyoxyalkylenes having hydrogenated end groups and/or hydrogenated repetitive units, as described in EP-625,526.

The amount of iodinated olefin of formula (I) to be added to the reaction mixture depends on the amount of units deriving therefrom which are intended to be obtained in the final product, bearing in mind that, at the low amounts employed according to the purposes of the present invention, practically the whole amount of the iodinated olefin present in the reaction medium enters the chain.

The polymerization reaction is generally carried out at a temperature of from 25° to 150° C., at a pressure up to 10 MPa.

When polymerization is completed, the fluoroelastomer is isolated from the emulsion by means of conventional methods, such as coagulation by addition of electrolytes or by cooling.

The peroxide curing is carried out, according to the art, by addition of a suitable peroxide capable of generating radicals by heating. Among the most commonly used we car cite:

dialkylperoxides, such as for instance di-tertbutyl-peroxide and 2,5-dimethyl-2,5-di(tertbutylperoxy)hexane; dicumyl peroxide; dibenzoyl peroxide; ditertbutyl perbenzoate; di[1,3-dimethyl-3-(tertbutyl-peroxy)butyl]carbonate. Other peroxide systems are described, for instance, in EP Patents 136,596 and 410,351.

To the cure mixture other products are then added, such as:

(a) curing coagents, in an amount generally from 0.5 to 10%, preferably from 1 to 7%; by weight with respect to the polymer; among them commonly used are: triallyl-cyanurate; triallyl-isocyanurate (TAIC); tris (diallyl-amine)-s-triazine; triallylphosphite; N,N-diallyl-acrylamide; N,N,N',N'-tetraallyl-malonamide; trivinyl-isocyanurate; 2,4,6-trivinyl-methyltrisiloxane, etc.; TAIC is particularly preferred.

(b) a metal compound, in an amount of from 1 to 15%, preferably from 2 to 10%, by weight with respect to the polymer, selected from divalent metal oxides or hydroxides, such as for instance Mg, Zn, Ca or Pb, optionally associated to a weak acid salt, such as for instance Ba, Na, K, Pb, Ca stearates, benzoates, carbonates, oxalates, or phosphites;

(c) other conventional additives, such as fillers, pigments, antioxidants, stabilizers, and the like.

As said above, the fluoroelastomers object of the present invention do not require long post-curing treatments; to remove possible volatile by-products, after curing it is sufficient to treat the product in air for 30–60 minutes at 180°–230° C. As demonstrated by the experimentation carried out by the Applicant, longer post-curing periods do not lead to any significant improvement of mechanical and/or elastic properties of the product. This allows to drastically reduce processing times, with consequent increase of productivity for molding processes on an industrial scale.

The present invention will be now better illustrated by the following working examples, whose purpose is merely indicative but not limitative of the scope of the invention itself.

EXAMPLE 1

Preparation of $CH_2=CH-(CF_2CF_2)_3-CH_2CH_2I$ (1) Ethylene Addition

In a 5 l AISI 316 steel reactor, equipped with a magnetic stirrer, previously evacuated and then brought to nitrogen atmosphere, were loaded: 1200 g (2.17 moles) of $I-(CF_2CF_2)_3-I$ (prepared as described in J. Fluorine Chemistry, 47 (1990), 199); 12.4 g of CuI; 2.2 l of acetonitrile. The reactor was then pressurized with 5.0 moles of ethylene, and brought to a temperature of 160° C., and kept at such temperature for 10 hours under stirring. The pressure reached a maximum of 51 ate and then gradually decreased up to 10 ate. The reactor was then cooled down to room temperature, and the unreacted ethylene was discharged. The reaction mixture, containing sediments, was discharged and, after pre-stirring with excess of water, filtered on a buchner at reduced pressure, and washed with water. The collected solid was dried in an oven at 110° C. 1300 g of product were so obtained, which at gaschromatographic analysis showed a sole peak (yield: 98%).

$^{19}$F-NMR and $^1$H-NMR analysis gave the following results:

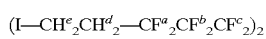

$^{19}$F-NMR (CDCl$_3$) a=−114.5 ppm; b=−123 ppm; c=−121 ppm; a/b/c=1/1/1

$^1$H-NMR e=2.7–3.0 ppm; d=3.4 ppm; e/d=1/1.

(2) Dehydroiodination

In a 500 ml glass reactor, equipped with a mechanical stirrer, a thermometer, a dropping funnel with compensator, a water-cooled claisen with a gathering flask kept at −15° C. (cold trap) were loaded: 80 g (0.131 moles) of $I-CH_2CH_2(CF_2CF_2)_3-CH_2CH_2I$ and 80 ml of diethylenglycol. The pressure in the system was reduced to 50 mmHg by means of a mechanical pump and the temperature brought to 130° C. by immersion in an oil bath. A solution consisting of 15 g of NaOH dissolved in 50 ml of H$_2$O was then gradually added (in about 30 min). Development of vapours, which condensed in the cold trap, revealed immediately that the reaction took place. At the end of the reaction, two phases were present in the cold trap, which were separated in a separating funnel. The aqueous phase was extracted with methylene chloride, which was then removed by distillation at reduced pressure. The so obtained organic phase and that left in the reactor were put together to give a total of 52.3 g of reaction products. By means of gaschromatography analysis, the mixture resulted to be formed by:

| | |
|---|---|
| $CH_2=CH-(CF_2CF_3)_3-CH=CH_2$ | 54% by weight |
| $I-CH_2CH_2-(CF_2CF_2)_3-CH=CH_2$ | 40% " |
| $I-CH_2CH_2-(CF_2CF_2)_2-CH_2CH_2-I$ | 6% " |

After fractional distillation, 20.3 g of iodinated olefin $I-CH_2CH_2-(CF_2CF_2)_3-CH=CH_2$ (purity: 99%; yield: 32%) were obtained.

Polymerization Reaction

In a 5 l autoclave equipped with a stirrer working at 630 rpm, were charged, after evacuation, 3.5 l of demineralized water and 36 ml of a microemulsion obtained by mixing:

7.8 ml of an acid terminated perfluoropolyoxyalkylene of formula:

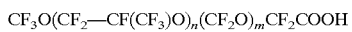

where n/m=10, having average molecular weight of 600;

8.9 ml of a 30% by volume NH$_4$OH aqueous solution;

15.6 ml of demineralized water;

4.8 ml of Galden$^{(R)}$ D02 of formula:

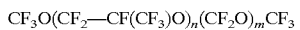

wherein n/m=20, having average molecular weight of 450.

The autoclave was then brought to 80° C. and kept at such temperature for the whole duration of the reaction. The following mixture of monomers was then fed:

| | |
|---|---|
| VDF | 24.0% by moles |
| HFP | 59.5% " |
| TFE | 16.5% " | so as to bring the pressure to 25 bar.

In the autoclave were then introduced:

112 ml of an aqueous solution of ammonium persulphate (APS) having a concentration of 1 g/l;

1,6-diiodoperfluorohexane (C$_6$F$_{12}$I$_2$) as chain transfer agent, in the form of a solution obtained dissolving 6.0 ml of the iodinated product in 14.0 ml of the same Galden(R) D02 used for the microemulsion; the addition was carried out in 20 portions, each portion of 1.0 ml, at the polymerization start and for each 5% increase in the monomer conversion;

the iodinated olefin of formula $CH_2=CH-(CF_2CF_2)_3-CH_2CH_2I$, in the form of a solution obtained dissolving 3.0 ml in 47.0 ml of the same Galden(R) D02 described above; the addition was carried out in 20 portions, each portion of 2.5 ml, at the polymerization start and for each 5% increase in the monomer conversion.

The pressure of 25 bar was kept constant for the whole duration of the polymerization by feeding a mixture consisting of:

| VDF | 50% by moles |
|---|---|
| HFP | 26% " |
| TFE | 24% " |

After 300 minutes of reaction, the autoclave was cooled, the latex drained and the polymer coagulated by addition of an aluminum sulphate solution (6 g of sulphate per liter of latex). After washing, the so obtained product was dried in an oven for 24 hours at 70° C. 1500 g of product were so obtained, which was characterized as reported in Table 1. The polymer monomer composition was determined by $^{19}F$-NMR analysis, the iodine percentage by X-ray fluorescence measurements. The osmometric average molecular weight ($M_n^{osm}$) was calculated, by calibration curves, from molecular weight values measured by Gel Permeation Chromatography (GPC).

The polymer was then peroxide cured: the vulcanization mixture composition and the characteristics of the cured product are reported in Table 2. It is to be noticed that, differently from the products of the prior art, a prolonged post-curing treatment (24 hours at 200° C.) did not lead to any improvement of mechanical and elastic properties of the cured product if compared with a shorter treatment (only 1 hour at 200° C.).

EXAMPLE 2

Example 1 was repeated, except that during the polymerization step 6 ml of the same iodinated olefin, dissolved in 94 ml of the same Galden(R) D02 were introduced in the reactor. The addition was carried out in 20 portions of 5 ml, at the reaction start and each 5% increase in the monomer conversion. The reaction was discontinued by cooling after 303 minutes, obtaining 1300 g of polymer. The characteristics of the product as such and after peroxide curing are reported in Tables 1 and 2, respectively.

EXAMPLE 3

Comparative

Following the same procedure as described in Example 1, a polymer of the same type but without the iodinated olefin was prepared. The properties of the product as such and after peroxide curing are reported in Tables 1 and 2, respectively.

TABLE 1

| EXAMPLE | 1 | 2 | 3(*) |
|---|---|---|---|
| Polymer composition (% mole) | | | |
| VDF | 53.9 | 55.6 | 54.0 |
| HFP | 20.3 | 19.9 | 21.5 |
| TFE | 25.9 | 24.5 | 24.5 |
| iodinated olefin | 0.06 | 0.13 | — |
| Total iodine | | | |
| (% weight) | 0.29 | 0.41 | 0.22 |
| (per chain) | 1.83 | 2.23 | 1.38 |
| Mooney Viscosity (ASTM D1646) ML (1 + 10') 121° C. | 46 | 32 | 45 |
| $M_n^{DSC}$ | 80,000 | 69,000 | 80,000 |
| $T_g$ onset (° C.) (DSC - ASTM D3418-82) | −13.4 | −13.5 | −12.0 |

(*)comparative

TABLE 2

| EXAMPLE | 1 | 2 | 3(*) |
|---|---|---|---|
| Vulcanization mixture composition | | | |
| Polymer (g) | 100 | 100 | 100 |
| Luperco(R) 101 XL (phr) | 3 | 3 | 3 |
| Drimix(R) TAIC ( " ) | 4 | 4 | 4 |
| ZnO ( " ) | 5 | 5 | 5 |
| Carbon black MT ( " ) | 30 | 30 | 30 |
| Vulcanization mixture characterics | | | |
| *Mooney Viscosity ML (1 + 10')¹²¹° C. (ASTM D1646) | 45 | 33 | 41 |
| *ODR 177° C. arc 3, 12' (ASTM D2084-81) | | | |
| ML (pounds · inch) | 11 | 7 | 10 |
| MH ( " ) | 141 | 147 | 124 |
| $t_{s2}$ (sec) | 51 | 51 | 57 |
| $t_{s50}$ ( " ) | 81 | 81 | 93 |
| $t'_{90}$ ( " ) | 117 | 114 | 115 |
| $V_{max}$ (pounds · foot · inch/sec) | 2.66 | 3.17 | 2.7 |
| Characteristics after curing in press at 170° C. for 10' (ASTM D412-83) | | | |
| Modulus at 100% (MPa) | 4.8 | 4.5 | 3.6 |
| Stress at break (MPa) | 17.3 | 16.7 | 17.2 |
| Elongation at break (%) | 226 | 215 | 295 |
| Shore A hardness (points) | 69 | 71 | 72 |
| Characteristics after post-curing in oven at 200° C. for 1 hour | | | |
| *MECHANICAL PROPERTIES (ASTM D412-83) | | | |
| Modulus at 100% (MPa) | 6.5 | 6.8 | 4.9 |
| Stress at break (MPa) | 21.2 | 20.4 | 20.7 |
| Elongation at break (%) | 205 | 196 | 273 |
| Shore A hardness (points) | 72 | 74 | 72 |
| *COMPRESSION SET (at 200° C. for 70 hours - ASTM D395 Method B) | | | |
| O-ring 214 (%) | 19 | 18 | 27 |
| Characteristics after post-curing in oven at 200° C. for 24 hours | | | |
| *MECHANICAL PROPERTIES (ASTM D412-83) | | | |
| Modulus at 100% (MPa) | 6.8 | 7.3 | 4.7 |
| Stress at break (MPa) | 21.1 | 20.0 | 19.2 |

TABLE 2-continued

| EXAMPLE | | 1 | 2 | 3(*) |
|---|---|---|---|---|
| Elongation at break | (%) | 198 | 192 | 272 |
| Shore A hardness | (points) | 72 | 74 | 72 |
| *COMPRESSION SET | | | | |
| (at 200° C. for 70 hours - ASTM D395 Method B) | | | | |
| O-ring 214 | (%) | 18 | 18 | 30 |

(*)comparative

EXAMPLE 4

In a 10 l autoclave, equipped with a stirrer working at 545 rpm, were loaded, after evacuation, 6.7 l of demineralized water and 66.9 ml of a microemulsion obtained by mixing:
  14.5 ml of an acid terminated perfluoropolyoxyalkylene of formula:

$CF_3O(CF_2-CF(CF_3)O)_n(CF_2O)_mCF_3COOH$ wherein n/m=10, having average molecular weight of 600;
  14.5 ml of a 30% by volume $NH_4OH$ aqueous solution;
  29.0 ml of demineralized water;
  8.9 ml of Galden$^{(R)}$ D02 of formula:

$CF_3O(CF_2-CF(CF_3)O)_n(CF_2O)_mCF_3$ wherein n/m=20, having average molecular weight of 450.

The autoclave was then brought to 80° C. and kept at such temperature for the whole duration of the reaction. The following monomer mixture was then fed:

| VDF | 64.5% by moles |
|---|---|
| MVE | 32.0% " |
| TFE | 3.5% " |

(MVE = perfluoromethylvinylether)
so as to bring the pressure to 25 bar.
  In the autoclave were then introduced:
    214 ml of a ammonium persulphate aqueous solution (APS) having concentration of 1 g/l,
    1,6-diiodoperfluorohexane ($C_4F_{12}I_3$) as chain transfer agent, in the form of a solution obtained by dissolving 7.6 ml of the iodinated product in 12.4 ml of the same Galden$^{(R)}$ D02 used for the microemulsion;
    the iodinated olefin of formula $CH_2=CH-(CF_2CF_2)_3-CH_2CH_2I$, in the form of a solution obtained by dissolving 5.0 ml in 95.0 ml of the same Galden$^{(R)}$ D02 described above; the addition was carried out in 20 portions, each portion of 5 ml, at the polymerization start and each 5% increase in monomer conversion.
  The pressure of 25 bar was kept constant for the whole duration of the polymerization by feeding a mixture consisting of:

| VDF | 75% by moles |
|---|---|
| MVE | 21% " |
| TFE | 4% " |

After 187 minutes of reaction, the autoclave was cooled, the latex drained and the polymer coagulated by addition of an aluminum sulphate solution (6 g of sulphate per liter of latex). After washing, the so obtained product was dried in an oven for 24 hours at 70° C. 2500 g of product were so obtained, which was characterized as reported in Table 3.
  The polymer was then peroxide cured: the vulcanization mixture composition and the characteristics of the cured product are reported in Table 4.

EXAMPLE 5

Comparative

Following the same procedure a described in Example 4, a polymer of the same type but without the iodinated olefin was prepared. The properties of the product as such and after peroxide curing are reported in Tables 3 and 4 respectively.

TABLE 3

| EXAMPLE | | 4 | 5(*) |
|---|---|---|---|
| Polymer composition (% mole) | | | |
| VDF | | 79.0 | 80.2 |
| HFP | | 17.0 | 15.7 |
| TFE | | 4.0 | 4.0 |
| iodinated olefin | | 0.05 | — |
| Total iodine | | | |
| (% peso) | | 0.30 | 0.26 |
| (per chain) | | 1.53 | 1.31 |
| Mooney viscosity (ASTM D1646) | | | |
| ML (1 + 10') | 121° C. | 28 | 28 |
| ML (1 + 4') | 100° C. | 52 | 58 |
| $M_n^{DSC}$ | | 65,000 | 64,000 |
| $T_g$ onset | (° C.) | −36.1 | −37.0 |
| (DSC - ASTM D3418-82) | | | |

(*)comparative

TABLE 4

| EXAMPLE | | 4 | 5(*) |
|---|---|---|---|
| Vulcanization mixture composition | | | |
| Polymer | (g) | 100 | 100 |
| Luperco$^{(R)}$ 101 XL | (phr) | 3 | 3 |
| Drimix$^{(R)}$ TAIC | ( " ) | 4 | 4 |
| ZnO | ( " ) | 5 | 5 |
| Carbon black MT | ( " ) | 30 | 30 |
| Vulcanization mixture characterics | | | |
| *Mooney Viscosity ML | | 30 | 33 |
| (1 + 10')$^{121° C.}$ | | | |
| (ASTM D1646) | | | |
| *ODR 177° C. arc 3, 12' (ASTM D2084-81) | | | |
| ML | (pounds · inch) | 7 | 7 |
| MH | ( " ) | 134 | 113 |
| $t_{s2}$ | (sec) | 51 | 57 |
| $t'_{s50}$ | ( " ) | 81 | 87 |
| $t'_{90}$ | ( " ) | 111 | 114 |
| $V_{max}$ | (pounds · foot · inch/sec) | 3.3 | 2.85 |
| Characteristics after curing in press | | | |
| at 170° C. for 10' (ASTM D412-83) | | | |
| Modulus at 100% | (MPa) | 3.4 | 2.6 |
| Stress at break | (MPa) | 14.5 | 13.5 |

TABLE 4-continued

| EXAMPLE | | 4 | 5(*) |
|---|---|---|---|
| Elongation at break | (%) | 236 | 324 |
| Shore A hardness | (points) | 66 | 64 |
| Characteristics after post-curing in oven at 200° C. for 1 hour | | | |
| *MECHANICAL PROPERTIES (ASTM D412-83) | | | |
| Modulus at 100% | (MPa) | 3.6 | 2.9 |
| Stress at break | (MPa) | 16.3 | 15.5 |
| Elongation at break | (%) | 237 | 292 |
| Shore A hardness | (points) | 67 | 66 |
| *COMPRESSION SET (at 200° C. for 70 hours - ASTM D395 Method B) | | | |
| O-ring 214 | (%) | 24 | 36 |
| Characteristics after post-curing in oven at 200° C. for 24 hours | | | |
| *MECHANICAL PROPERTIES (ASTM D412-83) | | | |
| Modulus at 100% | (MPa) | 6.8 | 4.7 |
| Stress at break | (MPa) | 21.1 | 19.2 |
| Elongation at break | (%) | 198 | 272 |
| Shore A hardness | (points) | 72 | 72 |
| *COMPRESSION SET (at 200° C. for 70 hours - ASTM D395 Method B) | | | |
| O-ring 214 | (%) | 22 | 33 |

(*)comparative

What is claimed is:

1. A peroxide curable fluoroelastomer having iodine atoms in a terminal position, and monomeric units in the chain deriving from an iodinated olefin of formula:

CHR=CH—Z—CH$_2$CHR—I    (I)

wherein:

R is —H or —CH$_3$; Z is a C$_1$–C$_{18}$ (per)fluoroalkylene radical, linear or branched, optionally containing one or mote ether oxygen atoms, or a (per)fluoropolyoxyalkylene radical, said fluoroelastomer obtainable by a copolymerization process of the monomers in an aqueous micro emulsion of perfluoropolyoxyalkylenes or of fluoropolyoxyalkylenes having hydrogenated end groups and/or hydrogenated repetitive units, in the presence of a radical initiator and an iodinated chain transfer agent.

2. The fluoroelastomer according to claim 1, wherein the iodinated chain transfer agent is a compound of formula R$_f$I$_x$, wherein R$_f$ is a (per)fluoroalkyl or a (per)fluorochloroalkyl having from 1 to 8 carbon atoms, and x is 1 or 2.

3. Fluoroelastomers according to claim 1, obtainable by a copolymerization process of the monomers in aqueous emulsion in the presence of a radical initiator and of an iodinated chain transfer agent.

4. Fluoroelastomers according to claim 3, wherein the iodinated chain transfer agent is a compound of formula R$_f$I$_x$, wherein R$_f$ is a (per)fluoroalkyl or a (per)fluorochloroalkyl having from 1 to 8 carbon atoms, while x is 1 or 2.

5. Iodinated olefins of formula (I), defined according to claim 1.

6. Process for preparing the iodinated olefins of claim 5, which comprises in sequence:

(1) adding ethylene or propylene to a compound of formula I—Z—I, to obtain a diiodinated product having the formula:

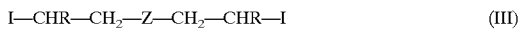

I—CHR—CH$_2$—Z—CH$_2$—CHR—I    (III)

wherein R and Z are defined as above;

(2) partially dehydroiodinating the product of formula (III) with a base so as to obtain the iodinated olefin of formula (I).

7. Process according to claim 6, wherein step (2) is carried out in defect of the base, and afterwards the iodinated olefin is separated by fractional distillation.

8. Process according to claim 6, wherein the step (2) is carried out at reduced pressure, so as to remove the iodinated olefin from the reaction mixture as it forms.

9. Process according to claim 6, wherein step (1) is carried out in defect of ethylene or propylene, so as to favour formation of mono-addition product I—Z—CH$_2$—CHR—I; the mono-addition product is then dehydroiodinated according to step (2), with formation of the olefin I—Z—CH=CHR, which is finally subjected to further addition of ethylene or propylene to give the iodinated olefin of formula (I).

* * * * *